United States Patent [19]

Picha et al.

[11] Patent Number: 5,080,654
[45] Date of Patent: Jan. 14, 1992

[54] FLUID INJECTION DEVICE FOR INTRAVENOUS DELIVERY SYSTEM

[75] Inventors: George J. Picha, Independence; Dean J. Secrest, Euclid; Steven L. Bernard, Cleveland, all of Ohio

[73] Assignee: Applied Medical Technology, Inc., Independence, Ohio

[21] Appl. No.: 610,469

[22] Filed: Nov. 8, 1990

Related U.S. Application Data

[63] Continuation of Ser. No. 408,621, Sep. 18, 1989, abandoned.

[51] Int. Cl.$^5$ .............................................. A61M 5/178
[52] U.S. Cl. .................................... 604/167; 604/256
[58] Field of Search ............... 604/256, 167, 168, 280, 604/283

[56] References Cited

U.S. PATENT DOCUMENTS

| | | | |
|---|---|---|---|
| 1,180,665 | 4/1916 | McElroy | 215/DIG. 3 |
| 2,656,335 | 10/1953 | Eisenstein . | |
| 3,552,441 | 1/1971 | Luhieich | 137/625.48 |
| 3,994,293 | 11/1976 | Ferro . | |
| 4,000,739 | 1/1977 | Stevens | 604/167 X |
| 4,063,555 | 12/1977 | Ulixder . | |
| 4,133,441 | 1/1979 | Mittlemen et al. | 215/247 |
| 4,197,848 | 4/1980 | Garrett et al. . | |
| 4,240,411 | 12/1980 | Hosono | 604/167 |
| 4,289,129 | 9/1981 | Turner . | |
| 4,294,249 | 10/1981 | Sheehan et al. . | |
| 4,421,123 | 12/1983 | Percarpio . | |
| 4,475,548 | 10/1984 | Muto | 604/167 |
| 4,496,348 | 1/1985 | Genese et al. | 604/167 |
| 4,626,245 | 12/1986 | Weinstein et al. | 604/167 |
| 4,655,752 | 4/1987 | Honkanen et al. | 604/167 |
| 4,798,594 | 1/1989 | Hillstead | 604/167 |
| 4,809,679 | 3/1989 | Shimonaka et al. | 604/167 X |

Primary Examiner—John D. Yasko
Attorney, Agent, or Firm—Pearne, Gordon, McCoy & Granger

[57] ABSTRACT

A fluid injection device for an intravenous delivery system that has an access port for insertion of liquid medication. The access port is sealed with a resilient, compressible closure element adapted to be forced into the port into a sealing condition. The closure element has a preformed central passage formed therein and is adapted to have a normal uncompressed condition and a sealing condition wherein the element is pressed into the access port to compress it sufficiently to close the passage. An elongated, hollow injection probe is used to penetrate the closure element through the preformed passage. The injection probe has a relatively blunt forward end so that when the probe penetrates the seal element, fluid to be administered may be delivered to the sterile interior through the probe.

5 Claims, 2 Drawing Sheets

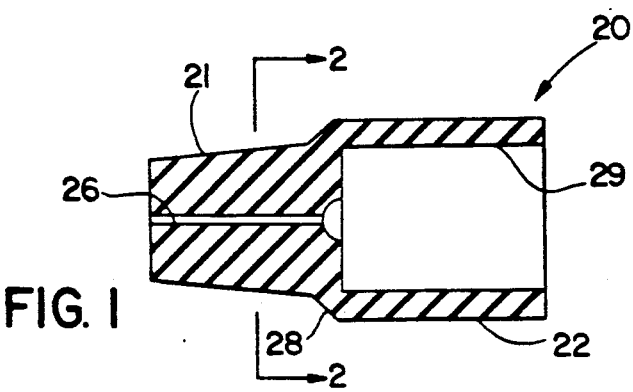
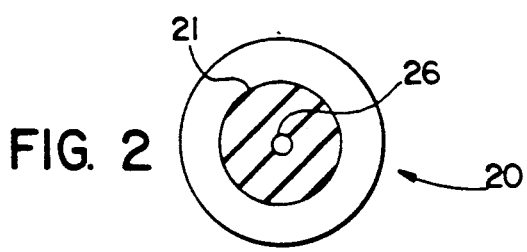
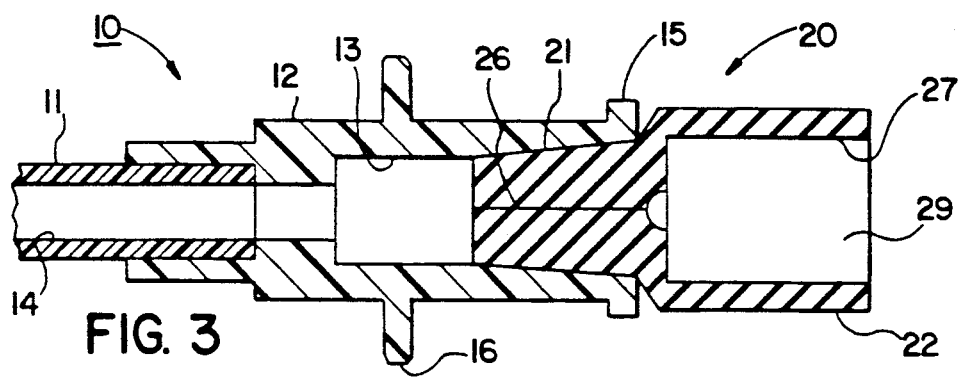
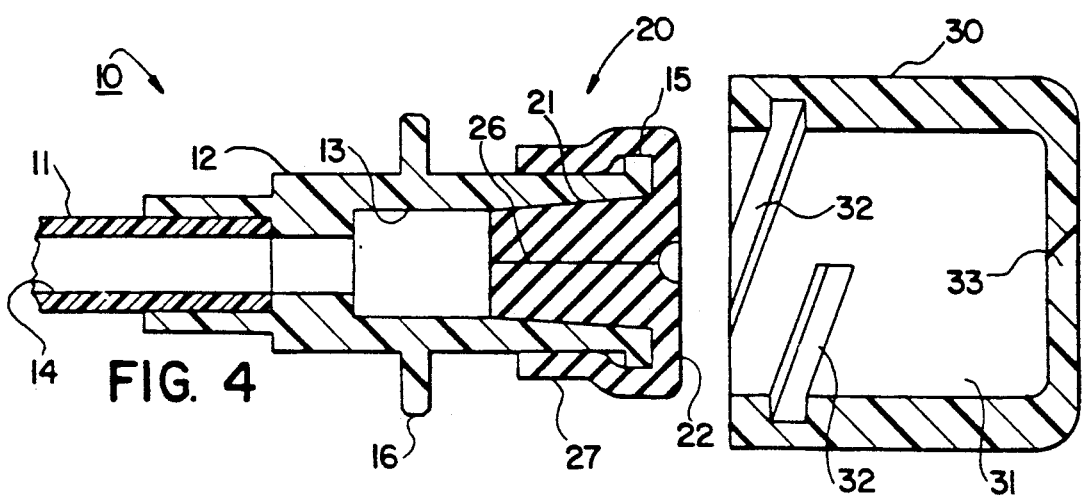

FLUID INJECTION DEVICE FOR INTRAVENOUS DELIVERY SYSTEM

This is a continuation of application Ser. No. 07/408,621, filed Sept. 18, 1989 now abandoned.

BACKGROUND OF THE INVENTION

This invention relates to medical equipment for the intravenous delivery of fluids to patients, and especially to a means for introducing a fluid from a container into the fluid passages of an enclosed sterile delivery system. More particularly, the invention relates to a means for penetrating a resealable membrane or barrier used to seal an access site in the system without requiring a sharp needle for the introduction of fluids.

Customarily, in hospitals and other medical treatment facilities, supplementary medications are administered via a hypodermic syringe through resealable, puncturable closures at access sites for intravenous delivery sets which transmit medication or fluid to the patient.

Sterile solutions are normally supplied to hospitals in sterile receptacles from which the solutions must be transferred to the sterile environment within the intravenous delivery set without introducing contaminants during the transfer process. This is typically accomplished by providing a fluid entry port or passage in the delivery set with a seal, such as an elastomeric plug or membrane, that serves as a barrier to external contaminants. The liquid to be introduced is then injected through a hollow needle with a sharp point adapted to pierce the barrier and enter the entry passage of the delivery set. When the needle is withdrawn, the elastomeric material reseals to preserve the sterile condition of both the solution being introduced and the interior of the intravenous delivery set.

While these prior art devices are effective in preserving the sterile environment required, the use of sharp needles presents a constant hazard to health care workers. In the medical field, there is an urgent need to minimize the risk of exposure of body fluids of health care workers to various types of contamination. One of the most common areas of exposure to this risk is in the administration of intravenous medication or other fluid. During this procedure, there are a number of ways in which the worker could inadvertently puncture his or her skin with a sharp hypodermic needle. Accidental skin puncture with contaminated or even sterile needles opens the body's immune defenses to a variety of viral infections. In particular, this type of event could expose the health care worker to acquired immune deficiency syndrome (AIDS), which is incurable—and usually fatal.

This invention seeks to eliminate this particular risk to health care workers. Accordingly, the fluid injection apparatus of the present invention reduces the problem described above and affords other features and advantages heretofore not obtainable.

SUMMARY OF THE INVENTION

It is among the objects of the present invention to provide an intravenous fluid delivery system that reduces, where possible, the use of sharp hypodermic needles to introduce medication into the delivery set.

Another object of the invention is to reduce the risk of viral and bacterial infection and the like to health care workers involved in the administration of intravenous medication.

Still another object is to reduce the risk of skin puncture (which occurs even through gloves) to health care workers.

A further object is to minimize the risk to health care workers of acquiring AIDS or hepatitis as a result of contaminants entering the body through skin punctures.

In accordance with the invention, there is provided a fluid injection apparatus for use with an intravenous delivery set which has an access port for insertion of liquid medication. The access port is sealed with a resilient, compressible closure element adapted to be forced into the port into a sealing position. The element has a preformed central passage formed therein and is adapted to have a normal uncompressed condition and a sealing condition wherein the element is pressed into the access port to compress it sufficiently to close the passage and seal the access port completely.

In accordance with the invention, a hollow injection probe is used to penetrate the element through the preformed passage. The injection probe has a relatively blunt forward end so that when the probe penetrates the plug and communicates with the sealed internal passage of the delivery set, the fluid to be administered may be delivered to the sterile interior through the probe.

BRIEF DESCRIPTION OF THE DRAWINGS

FIG. 1 is a sectional view showing an elastomeric closure element for use in sealing an access port in an intravenous delivery system and embodying the invention;

FIG. 2 is a transverse sectional view taken on the line 2—2 of FIG. 1;

FIG. 3 is a sectional view showing the closure element of FIG. 1 as initially inserted in the access port for an intravenous delivery system to seal the port;

FIG. 4 is a sectional view showing the next step in the sequence for connecting the closure element to the intravenous delivery system;

DESCRIPTION OF THE PREFERRED EMBODIMENT

Figure 5:
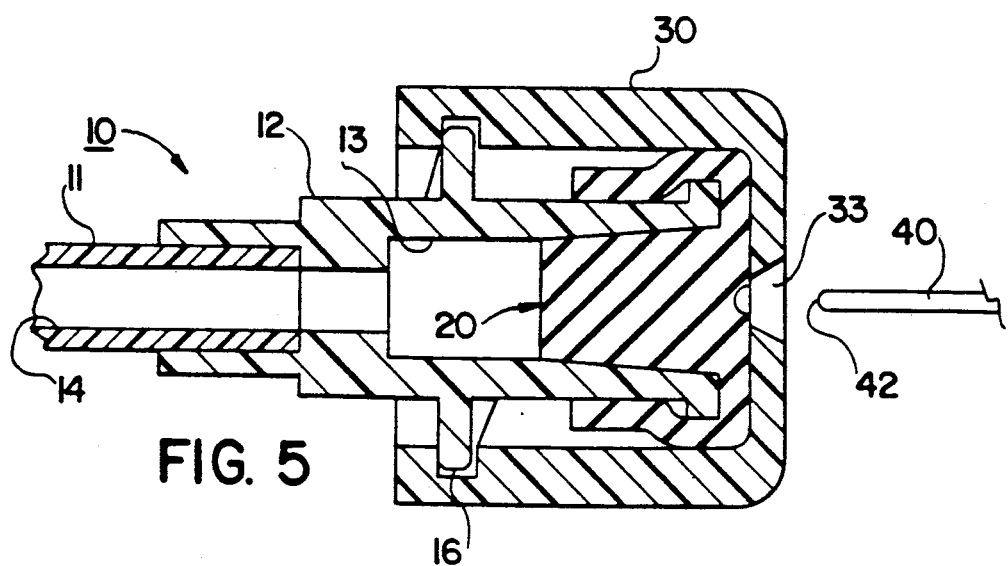
FIG. 5 is a sectional view showing the final step in the sequence for connecting and securing the closure element in place and also showing the end of the injection probe.

Referring more particularly to the drawings, there is shown access site 10 (FIGS. 3-6) for an intravenous delivery set which could be used for a variety of different applications. Typical applications would be for intravenous catheters of any type, Swan Ganz I. V.'s, heparin locks, tracheal balloons, and endotracheal balloons. The access site 10 is provided at the end of a catheter tube 11 or the like, which is connected to a nipple 12. The nipple 12 has an opening communicating with the passage 14 in the tube 11 and which provides an access port 13, a portion of which is outwardly tapered. The nipple 12 has a radial flange 15 formed on its outer end surrounding the access port 13. Also, the nipple 12 has a radially projecting helical rib 16 that provides an external thread, as will be described below.

In accordance with the invention, there are provided a seal device 20, to seal the access port 13 and to form a barrier against contaminants, and a thin, elongated injection probe 40 adapted to penetrate the seal device 20. The interior of the intravenous delivery set must be maintained in a sterile condition, as is well known in medical practice.

The seal device 20 comprises a generally cylindrical body with a tapered forward end 21 and a rearward end 22. The forward end functions as a plug and is adapted for insertion in the access port 13. The forward end or plug 21 is almost completely closed except for a small axial passage 26 that is formed therein either during initial molding or by means of a piercing instrument or the like. The diameter of the small passage 26 is less than the outer diameter of the injection probe 40, and furthermore is sufficiently small that when the plug 21 is pressed into the access port 13 of the nipple, and thereby radially compressed, the passage is closed so as to form a seal for the access port as well as a barrier against contamination.

The rearward end 22 of the seal 20 element has an enlarged diameter and is separated from the forward end by an annular shoulder 28. Also, the rearward end has a rather thin cylindrical wall 27 that defines a cylindrical chamber 29 (FIG. 3) that is coaxial with the preformed passage 26.

The assembly of the nipple 12 and the seal device 20, to include insertion of the plug portion 21 into the access port 13, is illustrated sequentially in FIGS. 3, 4, and 5. FIG. 3 shows the forward end or plug 21 of the seal device 20 inserted in the correspondingly tapered portion of the access port 13 to achieve radial compression that is sufficient to close the port 26. As shown in FIG. 3, however, the rearward portion 22 of the seal device 20 extends to the rear.

As shown in FIG. 4, however, an additional assembly step is taken by which the cylindrical wall 27 is rolled forwardly to fold the wall over the outer circumferential surface of the nipple. When this is done, the radial flange 15 of the nipple helps to secure the seal device due to the resiliency of the elastomeric material of the seal device.

The assembly of the device is completed by placing a cup-shaped cap 30 over the seal device 20, as illustrated in FIG. 5. The cap has an interior chamber 31 adapted to receive the seal element and the rearward portion of the nipple 12. Also, the cap is provided with an internal helical groove 32 that functions as an internal thread. The thread 32 engages the external thread 16 on the nipple 12 so that when the cap is rotated, the external thread of the nipple engages the internal thread of the cap to securely fasten the cap to the resulting assembly.

Figure 6:
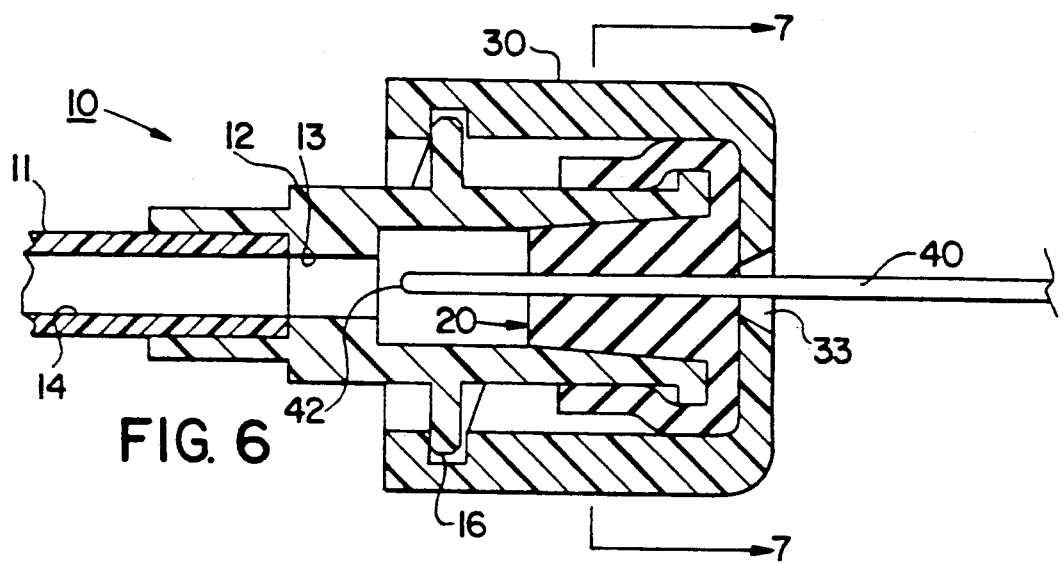
FIG. 6 is a sectional view illustrating the injection of medication into the delivery set by means of a hollow injection probe that has been forced through the closure element into the interior of the supply tube.
Figure 7:
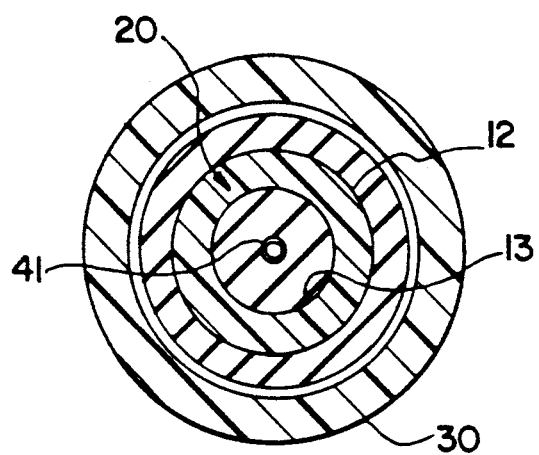
FIG. 7 is a transverse sectional view taken on the line 7—7 of FIG. 6.

The cap 30 has a tapered axial opening 33 extending therethrough at its rearward end to receive the injection probe 40, as shown in FIG. 6.

The seal element may be formed of a variety of moldable elastomers, such as a silicone rubber or a rubber latex material, the important property being sufficient compressibility to assure that the preformed passage 26 will be closed when the forward end 21 is pressed into the access port 13. The length of the preformed passage 26 should be sufficient to support and grip the injection probe 40 firmly when inserted, and the radial force against the injection probe resulting from the resilience of the elastomeric material should be sufficient to wipe the probe clean of any contaminants when it is inserted through the passage 26.

Other materials that may be used advantageously in the fabrication of the seal are natural rubber, polyurethane, isoprene, and styrene-butydine.

The injection probe 40 is an elongated, cylindrical, hollow metal implement, preferably formed of stainless steel, with an interior passage 41 extending completely therethrough to an axial opening at the forward end. The probe is supported in typical fashion in a syringe or at the ends of other I.V. tubing.

Most importantly, the forward end 42 or outer end of the probe is blunt, which distinguishes it from hypodermic needles and the like which the device of the present invention is intended to avoid. Accordingly, the forward end of the needle may be slightly rounded or otherwise blunted, the principal requirement being that the probe not be likely to pierce the skin of a health care worker in the event of accidental slippage or other inadvertence.

In operation, the intravenous delivery set is provided with an access site that includes an access port 13 closed by a seal element 20 embodying the invention and, more particularly, having a preformed axial passage 26 that is compressed into a closed sealing condition when the seal element 20 is pressed into the access port 13.

When a health care worker wishes to deliver a medication to the intravenous injection set (which already will have been placed in operation), he or she will take a syringe having an injection probe 40 embodying the invention and insert the forward end 42 of the probe through the end of the cap 30 until it engages the plug 21. Then the worker holds the cap with one hand and, with the other hand, forces the injection probe 40 into and through the preformed passage 26.

The resiliency of the material permits sufficient enlargement of the passage to accommodate the probe and, at the same time, the radial force, due to the resiliency of the material and the compression thereof, assures that any contamination on the probe will be wiped off during the injection movement.

As indicated above, the preformed passage 26 is sufficiently long that the injection probe is engaged over a significant portion of its length, so it is mechanically held and supported in correct axial alignment and also tightly gripped to prevent accidental removal.

After insertion of the probe is completed, the health care worker operates the syringe to inject the desired medication through the probe into the intravenous delivery set.

While the invention has been shown and described with respect to a specific embodiment thereof, this is intended for illustration rather than limitation, and other variations and modifications of the specific device shown will be apparent to those skilled in the art all within the intended spirit and scope of the invention. Accordingly, the patent is not to be limited in scope and effect to the specific embodiments herein shown and described, nor in any other way that is inconsistent with the extent to which the progress in the art has been advanced by the invention.

What is claimed is:

1. A fluid injection apparatus for use with an intravenous delivery set comprising:
   means in said delivery set defining an access port for injection of a fluid;
   a resilient, compressible closure element for sealing said access port and having a thin, elongated passage formed therethrough, said element having a normal uncompressed condition and a sealing condition wherein said element is tightly pressed into said access port to compress said element sufficiently to close said passage and seal said access port;

said closure element having a generally cylindrical shape and a rearwardly extending cylindrical wall that is adapted to be flexed radially outwardly and folded forwardly over an end portion of the means defining the access port; and a thin, elongated injection probe adapted to be forced through said axial passage when said element is in its sealing condition, said probe having a relatively blunt end, whereby said probe penetrates said seal element to permit injection of a fluid therethrough into said delivery set.

2. A fluid injection apparatus as defined in claim 1, further including a cap adapted to be tightly received over the folded end portion of said closure element and secured thereon, said cap having an end wall with a central opening therein adapted to receive and guide said injection probe.

3. A fluid injection apparatus as defined in claim 2, further including thread means on said cap and said means defining said access port respectively for threadedly securing said cap in position over said closure element.

4. A fluid injection apparatus for use with an intravenous delivery set and adapted for connection to a fluid source by means of an elongated injection probe having a relatively blunt end, comprising:

means in said delivery set defining an access port for injection of a fluid;

a resilient, compressible closure element for sealing said access port and having a thin, elongated passage formed therethrough, said element having a normal uncompressed condition and a sealing condition wherein said element is tightly pressed into said access port to compress said element sufficiently to close said passage and seal said access port;

said closure element having a generally cylindrical shape and a rearwardly extending cylindrical wall that is adapted to be flexed radially outwardly and folded forwardly over an end portion of the means defining the access port; and a cap adapted to be tightly received over the folded end portion of said closure elements and secured thereon, said cap having an end wall with a central opening therein adapted to receive and guide said injection probe;

whereby said probe may be forced through said axial passage when said element is in its sealing condition to permit injection of a fluid therethrough into said delivery set.

5. A fluid injection apparatus as defined in claim 4, further including thread means on said cap and said means defining said access port respectively for threadedly securing said cap in position over said closure element.

* * * * *